United States Patent
Novak et al.

(10) Patent No.: US 7,997,131 B2
(45) Date of Patent: Aug. 16, 2011

(54) DUAL-STRING DYNAMOMETER FOR MEASURING DENTAL HANDPIECE POWER AT HIGH SPEED AND LOW TORQUE

(75) Inventors: Eugene J. Novak, Deerfield, IL (US);
Tom Papanek, Lake Forest, IL (US);
Tadeusz Parafinczuk, Palatine, IL (US);
Todd Fanciullo, Lake Zurich, IL (US)

(73) Assignee: Dentsply International, Inc., York, PA (US)

( * ) Notice: Subject to any disclaimer, the term of this patent is extended or adjusted under 35 U.S.C. 154(b) by 0 days.

(21) Appl. No.: 12/750,778

(22) Filed: Mar. 31, 2010

(65) Prior Publication Data
US 2010/0326181 A1    Dec. 30, 2010

Related U.S. Application Data

(63) Continuation of application No. 12/215,835, filed on Jun. 30, 2008, now abandoned, which is a continuation of application No. 11/395,926, filed on Mar. 30, 2006, now abandoned, which is a continuation-in-part of application No. 11/022,092, filed on Dec. 22, 2004, now abandoned, which is a continuation of application No. 10/689,297, filed on Oct. 20, 2003, now abandoned.

(60) Provisional application No. 60/419,374, filed on Oct. 18, 2002.

(51) Int. Cl.
*G01L 5/04*    (2006.01)

(52) U.S. Cl. .............................. 73/160; 73/760; 73/826

(58) Field of Classification Search ................ 73/160, 73/760, 826
See application file for complete search history.

(56) References Cited

U.S. PATENT DOCUMENTS

| | | | |
|---|---|---|---|
| 1,435,082 A | 11/1922 | Reedy | |
| 1,605,079 A | 11/1926 | Simmons | |
| 1,730,974 A | 10/1929 | Higbee | |
| 3,023,615 A | 3/1962 | Bennett | |
| 3,192,768 A | 7/1965 | Hildebrandt | |
| 3,210,992 A | 10/1965 | Lacy et al. | |
| 3,354,711 A | 11/1967 | Saney | |
| 3,598,999 A | 8/1971 | Kofmeister | |
| 3,717,205 A | 2/1973 | Wilderman | |
| 3,829,052 A | 8/1974 | Flannelly | |
| 4,135,812 A * | 1/1979 | Kingsland | ............... 355/51 |

(Continued)

FOREIGN PATENT DOCUMENTS

EP    0295223    9/1991

(Continued)

OTHER PUBLICATIONS

Dyson et al, Torque, power and efficiency characterization of dental air turbine handpieces, Elsevier Journal of Dentistry 27 (1999), pp. 573-586.

*Primary Examiner* — Max Noori

(74) *Attorney, Agent, or Firm* — Douglas J. Hura; David A. Zourne; Leana Levin

(57) ABSTRACT

A dual-string tension dynamometer (1) utilizes two strings (10, 11) wrapped around approximately ninety degrees of a test wheel (12). The lateral forces (E, F) are balanced such that the total lateral force net value is zero. The results reflect purely torsional loading.

4 Claims, 1 Drawing Sheet

U.S. PATENT DOCUMENTS

| | | | |
|---|---|---|---|
| 4,137,974 A | | 2/1979 | Decker |
| 4,148,218 A | | 4/1979 | Knowles et al. |
| 4,236,696 A | * | 12/1980 | Hicks et al. .................. 254/297 |
| 4,545,543 A | | 10/1985 | Plucknett |
| 4,632,388 A | * | 12/1986 | Schleffendorf .............. 482/102 |
| 4,856,325 A | | 8/1989 | Tomita et al. |
| 4,939,939 A | | 7/1990 | Vemmer |
| 4,960,001 A | | 10/1990 | Vemmer |
| 4,973,291 A | | 11/1990 | Mottate |
| 5,063,676 A | | 11/1991 | Gerber |
| 5,076,104 A | | 12/1991 | Glaesemann et al. |
| 5,150,799 A | | 9/1992 | Long, Jr. |
| 5,282,580 A | | 2/1994 | Kent |
| 5,335,527 A | | 8/1994 | Nagal et al. |
| 5,540,041 A | | 7/1996 | Campbell et al. |
| 5,667,465 A | | 9/1997 | McCollum et al. |
| 5,945,602 A | | 8/1999 | Ross |
| 5,957,359 A | | 9/1999 | Paivinen |
| 6,032,448 A | * | 3/2000 | Baker et al. ....................... 57/10 |
| 6,311,805 B1 | | 11/2001 | Juan |
| 2005/0042588 A1 | * | 2/2005 | Wallaker ....................... 434/262 |
| 2007/0113699 A1 | * | 5/2007 | Khajepour et al. ........ 74/490.03 |

FOREIGN PATENT DOCUMENTS

| | | |
|---|---|---|
| JP | 06109565 | 4/1994 |
| WO | 2004036167 A2 | 4/2004 |

* cited by examiner

DUAL-STRING DYNAMOMETER FOR MEASURING DENTAL HANDPIECE POWER AT HIGH SPEED AND LOW TORQUE

RELATED APPLICATIONS

This application is a Continuation of U.S. Ser. No. 12/215,835 filed on Jun. 30, 2008 now abandoned, which is a Continuation of U.S. Ser. No. 11/395,926 filed on Mar. 30, 2006 now abandoned which is a Continuation-in-Part of U.S. Ser. No. 11/022,092 filed on Dec. 22, 2004 (now abandoned) which was a Continuation of U.S. Ser. No. 10/689,297 filed Oct. 20, 2003 now abandoned, which claims the benefit of U.S. Provisional Application Ser. No. 60/419,374 filed on Oct. 18, 2002.

TECHNICAL FIELD

The present invention is generally related to string tension dynamometers used to measure power in a high speed, low torque dental handpiece. More particularly, the invention relates to such a dynamometer employing dual or two strings in order to avoid a lateral force being exerted on the test wheel. The lateral forces are balanced resulting in a total lateral force net value of zero.

BACKGROUND OF THE INVENTION

The power output of high-speed, low torque dental handpieces, such as air turbine handpieces, can be measured using a string tension dynamometer. For example, it is known to use a Kerfoot string tension dynamometer, which is a device that applies a load to a handpiece through a string looped around a pulley mounted in a handpiece chuck (See FIG. 1). With a Kerfoot device, string tension is measured by the deflection of weighted dials to which the ends of the string are attached. Under steady-state conditions, the net tension on the string multiplied by the pulley radius is equal to the handpiece torque.

According to one test protocol, the face of the pulley is half blacked out for speed detection using an optical tachometer. The pulley shaft conforms to DIN 13950 and ISO 1797 (0.0628", 1.595 millimeters diameter). The pulley wheel is lightweight aluminum, unconcentricity not more the 0.0003 inches. Each pulley is tested for balance at speeds up to 500,000 RPM by recording the free spin RPM of a new handpiece with each pulley and discarded if they are statistical outliers. The maximum power output of a handpiece occurs at a speed that is about half the no-load (or free-running) speed. To determine the power output, the maximum speed and the torque at half the maximum speed is measured. Torque and power can be measured as follows:

$P = vT$, where $v = RPM (2\pi)/60$ and $T = (T_R - T_L)mgR$

P is the power in Watts.
v is the speed expressed as angular velocity, radians per second.
RPM is the speed in revolutions per minute at which the torque was measured.
$\pi$ is the constant 3.14159.
T is the torque expressed as Newton-meters.
TR and TL are the right and left dial deflection readings (See FIG. 1).
m is the mass of the dial weights expressed in kilograms.
g is the gravitational acceleration, about 9.8 meters per second$^2$.
R is the pulley radius in meters (such as for example, 0.100" or $2.54 \times 10^{-3}$ meters). The actual pulley radius is adjusted to compensate for the thickness of the string. The effective pulley radius including the radius of the string is 0.100".

While such dynamometers have proven valuable in determining power, they do result in a small lateral force being exerted on the test wheel. Therefore, a purely torsional load never exists resulting in increased measurement error. A need exists therefore, for a string tension dynamometer which will avoid the torsional load-induced errors.

SUMMARY OF THE INVENTION

A dual-string tension dynamometer according to the present invention utilizes two strings. The lateral forces are balanced such that the total lateral force net value is zero. The results reflect purely torsional loading.

PREFERRED EMBODIMENT FOR CARRYING OUT THE INVENTION

A single-string dynamometer works on the premise that the tension difference between two sides of a load string equals the force applied to a test wheel at that specific radius. By summing vectors a resultant vector is found. This resultant cannot be zero due to the nature of the dynamometers operation. Additionally, this vector may include an orthogonal component if the load string is not mounted tangent to the test wheel. According to the present invention, adding a second string introduces a second set of forces. By keeping appropriate tension magnitudes equal, a zero net force results. A state of purely torsional loading has been reached.

Figure 2:
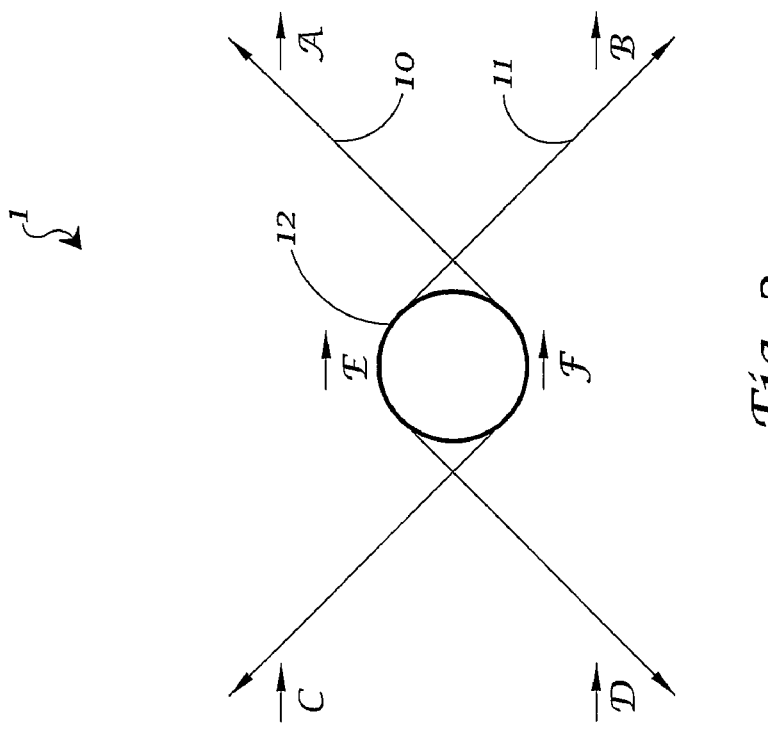
FIG. 2 is a schematic representation of a dual-string tension dynamometer according to the present invention.
Figure 1:
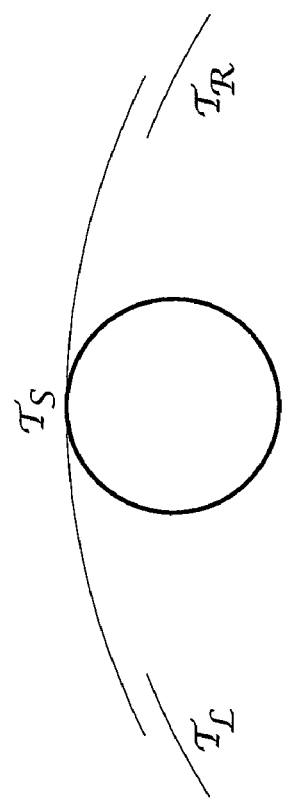
FIG. 1 is a schematic representation of a Prior Art single string tension dynamometer, showing the left and right dial deflection readings as $T_L$ and $T_R$ respectively. The force vector representing tension at $T_s$ is equal to the sum of $T_L$ and $T_R$.

A dual-string dynamometer 1 according to the invention includes two filaments 10 and 11, wrapped around approximately fifteen degrees to as much as three hundred sixty (substantially completely) or even more of a test wheel 12. A preferred embodiment has filaments 10 and 11 wrapped at about ninety degrees of test wheel 12. A conventional control device (not shown) may be introduced to maintain equal tensions and a zero lateral load. An example of such a control device may be a stepper motor at each string end to adjust string tension and a load cell to monitor string tension and that all four string ends are simultaneously controlled and measured by electronics and computer. Power values are determined by multiplying torque values with angular speed data. Such relationships are expressed according to the following equations, where A, B, C, D, E and F are force vectors at indicated points of the filaments 10 and 11 as shown on FIG. 2.

$$E = A + C$$

$$F = B + D$$

$$E + F = 0$$

A is the tension on one end of string 10; B is the tension on a same side of string 11; C is the tension on the other side of string 10 from A; D is the tension on the other side of string 11 from B; as is shown representationally in FIG. 2.

A dual-string dynamometer 1 as described eliminates lateral loading, which provides loading condition certainty. High speed, low torque power data can be accurately attained in an otherwise conventional manner. It will be appreciated that inventive dynamometer 1 as described allows one to independently control the lateral force and torsional loading applied to the test wheel and therefore to the test specimen such as, for example, a dental handpiece or other device under test. In actual use, the rotary cutting tool (bur) of a dental handpiece is subject to lateral forces and it may be desirable to measure how operation is affected by these lateral forces. This control of lateral and torsional forces is accomplished by independently controlling and monitoring the tensions (forces A, B, C, D) at each of the four string ends. It is further to be appreciated that an advantage of the present invention is that it can measure a test specimen such as a dental handpiece speed and torsional load at as many points as desired over the specimen's full operating range, thereby allowing a complete analysis of torque and power versus speed.

It will be appreciated that according to the present invention, any arrangement using two strings could be used. String wrap angle, wheel size, and string material can be altered in order to accommodate testing situations. Any means of controlling string tension could be used with varying degrees of accuracy. Further, while such a device is especially useful in testing dental high speed, low torque handpieces, such a device has application to any number of applications. It has been described herein with respect to the testing of dental handpieces only for exemplary purposes and should not necessarily be so limited. The invention is limited only by the scope of the attached claims.

What is claimed is:

1. A string tension dynamometer comprising a test wheel, a first filament wrapped around said test wheel and a second filament wrapped around said test wheel; wherein said first and said second filaments are wrapped around said test wheel on substantially opposite sides thereof; wherein lateral forces on said first and said second filaments are substantially balanced such that the total lateral force net value is substantially zero.

2. A string dynamometer as in claim 1, wherein said first filament and said second filament are independently wrapped around said test wheel to form an angle greater than or equal to about 15 degree angle.

3. A string dynamometer as in claim 2, wherein said first filament is wrapped around said test wheel to form about a 90 degree angle.

4. A string dynamometer as in claim 3, wherein said second filament is wrapped around said test wheel to form about a 90 degree angle.

* * * * *